US006791462B2

(12) United States Patent
Choi

(10) Patent No.: US 6,791,462 B2
(45) Date of Patent: Sep. 14, 2004

(54) SLEEPY ALARM SYSTEM ACTIVATED BY HEART PULSE METER

(76) Inventor: Sang J. Choi, 2425 W. 183rd St., Homewood, IL (US) 60430

( * ) Notice: Subject to any disclaimer, the term of this patent is extended or adjusted under 35 U.S.C. 154(b) by 0 days.

(21) Appl. No.: 10/245,582

(22) Filed: Sep. 18, 2002

(65) Prior Publication Data

US 2004/0051642 A1 Mar. 18, 2004

(51) Int. Cl.[7] .......................... G08B 23/00; A61B 5/02

(52) U.S. Cl. ....................... 340/575; 340/576; 600/301; 600/500

(58) Field of Search ................................ 340/575, 576; 600/301, 500

(56) References Cited

U.S. PATENT DOCUMENTS

| | | | |
|---|---|---|---|
| 4,280,506 A | | 7/1981 | Zurchar et al. |
| 4,305,401 A | | 12/1981 | Reissmueller et al. |
| 4,332,258 A | | 6/1982 | Arai et al. |
| 4,425,921 A | | 1/1984 | Fujisaki et al. |
| 4,467,285 A | | 8/1984 | Rinaldi |
| 4,610,257 A | | 9/1986 | Furukawa |
| 4,704,036 A | | 11/1987 | Holte et al. |
| 5,475,725 A | | 12/1995 | Nakamura |
| 5,488,353 A | * | 1/1996 | Kawakami et al. ......... 340/576 |
| 5,574,641 A | * | 11/1996 | Kawakami et al. ............ 701/1 |
| 5,791,347 A | | 8/1998 | Flaherty et al. |
| 5,807,267 A | * | 9/1998 | Bryars et al. ............... 600/500 |
| 5,810,736 A | | 9/1998 | Pail |
| 5,907,282 A | * | 5/1999 | Tuorto et al. ............... 340/575 |
| 6,213,954 B1 | | 4/2001 | Chen |
| 6,239,707 B1 | * | 5/2001 | Park ........................... 340/576 |
| 6,265,978 B1 | * | 7/2001 | Atlas .......................... 340/575 |

* cited by examiner

*Primary Examiner*—Jeffery Hofsass
*Assistant Examiner*—Anne V. Lai

(57) ABSTRACT

This invention provides a sleepy alarm apparatus for a vehicle driver, which is activated by a heart pulse meter, of which the measured heart pulse rate is lower than the preset threshold sleepy pulse rate. When a driver is sleepy while driving, the pulse rate is gradually decreasing. This invention continuously monitors the time interval for the predetermined number of the driver's pulses and converts the time interval into a pulse rate. If the measured pulse rate is lower than the preset threshold pulse rate, the system will trigger an alarm unit, which is a part of the present invention. The preset threshold pulse rate can be adjusted by the increase or decrease switch. The apparatus may be made to be wearable on a wrist or made to be attachable on the steering wheel of the vehicle being driven. In which case, the device includes a cuff for placing a finger in it in order to monitor the heart pulses.

8 Claims, 1 Drawing Sheet

SLEEPY ALARM SYSTEM ACTIVATED BY HEART PULSE METER

FIELD OF INVENTION

This invention relates to a sleepy warning system which is constantly monitoring a driver's pulse rate and activates an alarm means if the monitored pulse rate falls below a predetermine level.

BACKGROUND

A vast percentage of automobile accidents are attributed to sleepy driving. Many attempts have been made to develop a warning device which is activated when the driver becomes sleepy. One such device is made of a yoke, a pressure sensor and a sound device, which is worn around one's neck. The operation of the device is as following: when the driver feels sleepy, his head bents over on the yoke pressing the pressure sensor and the pressed sensor activates the sound device. However, wearing the device around the neck is very cumbersome, and placing the pressure sensor on the position where the head falls is very inconvenient.

Another inventor has tried to develop a drowsy alert system by applying a video sensor which is monitoring eyes opening. When the sensor monitors eyes closing for a couple seconds, it triggers the alert system. For many reasons, it has not been successful yet. In light of the importance of accident prevention for a vehicle, developing a reliable, convenient, and affordable sleep warning device is the prime objective of this invention.

SUMMARY

This invention is relating to a sleepy warning apparatus which comprises a pulse sensor, a measuring device and a warning device. A pulse rate is affected by the many variables. Each individual's pulse rate is different from one person to another. For the same person, the pulse varies depending upon how physically active the person is. The normal pulse rates for ordinary people are somewhere between 50, to 85. Another aspect to change pulse rate is the state of sleepiness.

For the most people, sleepy pulse rate is somewhere between 55, to 65. For the illustration purpose of this embodiment, when the start switch is pressed from off state, it sets threshold pulse rate to 60 (example) and stores it in a memory or a register, and starts measuring time interval for the predetermined number of pulse count, then converts this time interval to the pulse rate. Repeat this process continuously. Every newly measured pulse rate is compared to the threshold pulse rate, and if it is lower than the threshold pulse rate, it will trigger the alarm system.

The threshold pulse rate can be adjusted experimentally by INCREASE switch or DECREASE switch. Every push of these switches either increases or decreases the pulse rate by one. If the alarm is triggered while not quite sleepy, the threshold pulse rate can be decreased by pushing the DECREASE switch repeatedly, same number of times as the number to be adjusted. If the alarm feature is not triggered even if the person is sleepy, the pulse rate can be increased by pushing INCREASE switch repeatedly, same number of times as the number to be adjusted. Thus, the threshold pulse rate is determined by 2 different steps:

1) upon start switch pressed, the threshold number is set to 60 as default.
2) the threshold number can be either increased or decreased by the INCREASE switch or DECREASE switch.

If the pulse detector has not received any input pulse for 2 minutes period, the system get into sleep mode to save the battery consumption. During sleep mode, the system keeps the last held threshold number and last measured pulse rate in a memory. When the WAKEUP switch is pushed, the sleep pulse rate can be adjusted. Once the system is waked up by WAKEUP_switch, it will stay waked up as long as there is continuous pulse input. The system can be combined with a real clock function. The WAKEUP switch allows data display function, and preset threshold sleepy pulse adjustment function.

The system can be wearable on a wrist or attachable on a steering wheel of a vehicle with an additional cuff for placing a finger in it to monitor the pulse rate. The cuff includes the pulse sensor means. The system includes 4 externally activated switches, start switch, wakeup switch, increase switch, and decrease switch. Start switch turns the system off completely or turns it on to start from reset procedure. On the other hand, wakeup switch is used to wake up from the sleepy function for display function, and preset threshold sleepy pulse adjustment function.

BRIEF DESCRIPTION OF THE DRAWINGS

The following drawings will help those skilled in the art understand the objectives, functions, and structures of the present invention.

DETAILED DESCRIPTION OF THE PREFERRED EMBODIMENT

Figure 1:
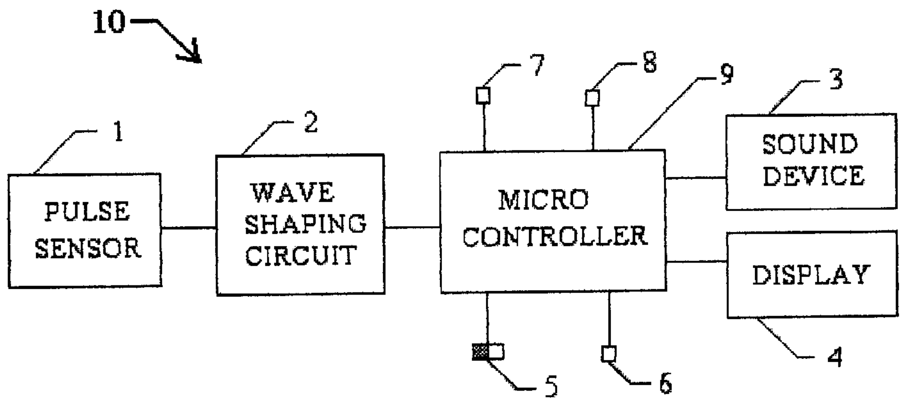
FIG. 1 shows a circuit block diagram of the present invention.

Referring to FIG. 1, a block diagram (10) is shown for the embodiment of this invention. The pulse sensor (1) monitors heart beat pulses and applies the sensed pulses to the waveshaping circuit (2) which converts the irregular input pulse wave to a square wave.

The microcontroller (9) receives the square waves, counts them, measures time interval, sets a threshold number, compares the measured pulse rate with the threshold pulse rate, generates alarm trigger signal if the measured pulse rate is lower than the threshold pulse rate, and displays the measured pulse rate and the threshold pulse rate.

Four switches, Start (5), wakeup (6), increase (7), and decrease (8) switches are connected to the microcontroller (9). Start switch (5) has 2 positions, ON and OFF. If the switch (5) is moved to ON position, the system starts processing from the beginning. It sets the sleepy threshold pulse rate to 60 as default, and processes the aforementioned functions. The normal pulse rate is different from one person to another.

While a person is sleepy, if the system does not trigger the alarm, the threshold pulse rate can be increased by pressing the INCREASE switch (7). On the other hand, while a person is not sleepy, if the alarm is activated, the threshold pulse rate can be decreased by pressing the DECREASE switch (8). For both switches, each pressing makes the respective change by one. By programming, the threshold limit rate can be set. (example from 53 to 67). If the system does not receive pulse input for 2 minutes while the power is still on, it will get into a sleep mode and drop power consumption drastically while keeping all necessary data. Later, when it is ready to use the system again, just press the wakeup switch (6). Then everything starts from where it stopped when getting in sleep function. The Wakeup switch provides 3 functions. When the system is started by Start switch (5), it will get in display function where current pulse rate, preset threshold sleep pulse rate, and current time are displayed. Next pushing the Wakeup switch again puts the system in the sleepy pulse rate adjustment function where the sleepy rate can be adjusted with the INCREASE switch (7) or DECREASE switch (8). Another pushing the Wakeup switch (6) puts the system in time adjustment function where the current time can be adjusted with the INCREASE switch (7) or DECREASE switch (8). Another pushing the Wakeup switch brings back to the normal display function.

Sound unit (3) generates a warning sound when activated by the warning signal from the microcontroller (9). Display unit (4) displays a pulse rate and flashing heart symbol, and a sleepy threshold pulse number. While the system is in sleep function, the display shows just a blank screen.

Figure 2:
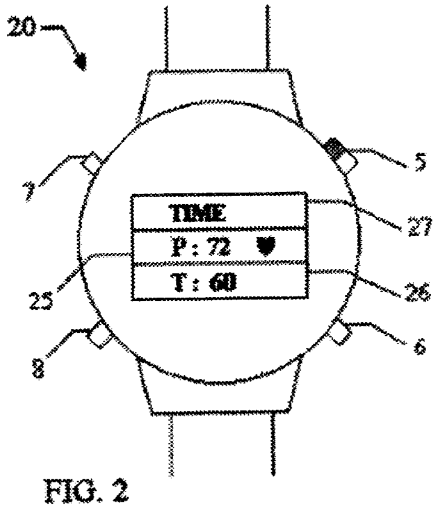
FIG. 2 shows a physical top view of the present invention.

Referring to FIG. 2, it shows a top view (20) of the present invention. The functions of start switch (5), wakeup switch (6), increase switch (7), and decrease switch (8) are the same as described in the FIG. 1. Pulse rate display (25) displays the most recently measured pulse rate. The flashing heart symbol indicates that the system is actively monitoring heart beat pulse. Threshold number display (26) displays the preset sleepy threshold pulse number, which is initially set by the system program and adjusted by the increase, decrease switches, and time display (27) displays the current time.

Figure 3:
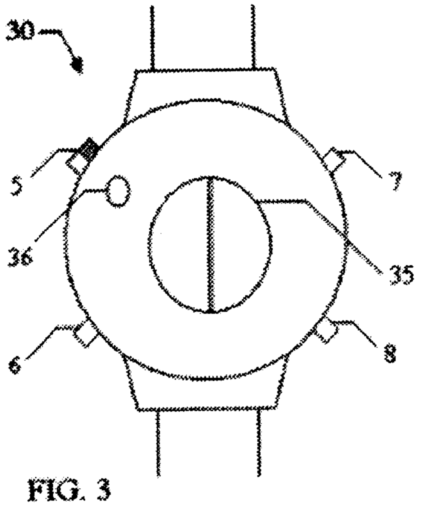
FIG. 3 shows a physical bottom view of the present invention.

Referring to FIG. 3, it shows a bottom view (30) of the present invention. The functions of Start switch (5), wakeup switch (6), increase switch (7), and decrease switch (8) are the same as described in FIG. 1. Sensor unit (36) is physically positioned sitting on the artery. Battery cover (35) holds a battery secured in place. The system can be made to be wearable on a wrist or made to be attachable on the steering wheel.

In the broader aspects, this invention is not limited to the specific embodiment illustrated and described herein. Those skilled in the art may make various changes and modifications without departing from the scope and sprit of the present invention. It is the expressed intention of this invention to embrace all such changes and modifications which fall within the scope of the described claims thereby.

What is claimed is:

1. A sleepy alarm system activated by detecting a lower pulse rate than a preset threshold sleepy pulse rate for a vehicle driver, of which a value is initially set for an average human pulse rate expected while a person is sleepy, and fine adjusted for the preset threshold sleepy pulse rate of the driver, comprising: a heart pulse meter; an alarm unit; an INCREASE switch and a DECREASE switch to fine adjust the preset threshold sleepy pulse rate; and a wakeup switch to invoke either sleepy pulse rate adjustment function, or normal display function.

2. A sleepy alarm system according to claim 1, wherein the heart pulse meter further comprises:

a) a pulse sensor to input a pulse signal;

b) a waveshaping circuit to shape input signal to a square wave;

c) a microcontroller for continuously;

measuring a time interval of every predetermined number of pulses, converting the measured time interval to a pulse rate, setting an initial threshold sleepy pulse rate, comparing the measured pulse rate with the preset threshold sleepy pulse rate, generating a warning signal if any comparison result shows that the measured pulse rate is lower than the preset threshold sleepy pulse rate; and d) a display unit to display: the measured pulse rate, flashing heart image, and the preset threshold sleepy pulse rate.

3. A sleepy alarm system according to claim 1, wherein the alarm unit generates a warning sound when activated.

4. A sleepy alarm system according to claim 1, wherein the increase switch and the decrease switch are used to adjust the threshold sleepy pulse rate.

5. A method of generating a warning sound when a measured pulse rate of a vehicle driver is lower than a preset threshold sleepy pulse rate, which is initially set for a value of an average human pulse rate expected while a person is sleepy, and fine adjusted for the sleepy pulse rate of a specific person or the driver by INCREASE or DECREASE switch.

6. A method of generating a warning sound according to claim 5, wherein the method further comprises the following steps:

a) adjusting a threshold sleepy pulse rate with the INCREASE and DECREASE switches;

b) continuously measuring the time intervals for every predetermined number of pulses, and converting the measured time interval to a newly measured pulse rate;

c) continuously comparing every newly measured pulse rate with the preset threshold sleepy pulse rate; and d) generating a warning sound if any comparison result shows that the newly measured pulse rate is lower than the preset threshold sleepy pulse rate.

7. A sleepy alarm system according to claim 1, a real time clock function can be combined in the alarm system.

8. A sleepy alarm system according to claim 1, wherein the WAKEUP switch provides the preset threshold sleepy pulse rate adjustment function, time adjustment function, and normal display function.

* * * * *